United States Patent [19]
Patterson, Sr. et al.

[11] Patent Number: 5,623,107
[45] Date of Patent: Apr. 22, 1997

[54] WHEEL DOVETAIL SCANNER

[75] Inventors: Robert W. Patterson, Sr., Cobleskill; Dennis E. Lessard, Waterford, both of N.Y.

[73] Assignee: General Electric Co., Schenectady, N.Y.

[21] Appl. No.: 446,159

[22] Filed: May 22, 1995

[51] Int. Cl.⁶ .................................................. G01M 19/00
[52] U.S. Cl. ........................................ 73/865.8; 73/866.5
[58] Field of Search .................................. 73/865.8, 866.5

[56] References Cited

U.S. PATENT DOCUMENTS

| | | | |
|---|---|---|---|
| 2,596,322 | 5/1952 | Zumwalt | 73/265.8 |
| 4,843,896 | 7/1989 | Napeloni et al. | 73/866.5 |
| 5,105,658 | 4/1992 | Jaafar et al. | 73/865.8 |
| 5,454,276 | 10/1995 | Wernicke | 73/865.8 |
| 5,481,929 | 1/1996 | Kohlert et al. | |

OTHER PUBLICATIONS

"A Compendium of Robotic Equipment Used in Hazardous Environments" EPRI NP-6697, Project 2519-1, Final Report, Feb. 1990, pp. 2-28/29, 5-14/15, 5-22/23, 5-26/27, 5-30/31.

*Primary Examiner*—Mark Hellner
*Attorney, Agent, or Firm*—Nixon & Vanderhye

[57] ABSTRACT

An inspection device having electric motor driven magnetic wheels for magnetic attachment of the device to the cylindrical surface between the wheels of a turbine rotor. The inspection device includes a mast that supports an ultrasonic transducer and a rotary encoder.

17 Claims, 3 Drawing Sheets

WHEEL DOVETAIL SCANNER

TECHNICAL FIELD

The invention relates to a scanner for rotating about a turbine rotor shaft or wheel hub to perform an ultrasonic inspection of wheel bucket attachment points.

BACKGROUND PRIOR ART

Turbine rotors have wheels provided with dovetail constructions, referred to as dovetails, at which point the wheel buckets are attached. The dovetails require inspection or examination for flaws. Standard inspection procedures for the dovetails have involved rotating the rotor. Rotating the rotor is a conventional part of the procedure for inspecting non integral rotors, i.e., rotors where the turbine wheels have been shrunk on the rotor shaft. That is, the inspection of the shrink interface is done while rotating the rotor, which is usually achieved by mounting and spinning the rotor on power roller equipment. Inspecting the dovetails of non-integral rotors by a procedure that involves rotating the rotor is readily facilitated since the rotor rotating equipment is available.

Automated ultrasonic test systems for detecting flaws in turbine wheel dovetails for use in conjunction with the rotation of the rotor by the power roller equipment have been developed. In general, these test systems include an optical encoder placed on either the turbine rotor shaft or the power roller equipment and the use of position data derived from the optical encoder for triggering ultrasonic pulses from a transducer at regular intervals. The ultrasonic test system acquires the data in polar format and plots signals in a B-scan display.

In the above described wheel dovetail inspection system the ultrasonic transducer is required to be positioned at a precise radial location on the wheel and remain at that location throughout 360 degrees rotation of the turbine rotor. A fixed manipulator or transducer holder with several axes of motion for alignment purposes is employed for precisely locating the transducer.

SUMMARY OF THE INVENTION

The invention provides a scanner for scanning the dovetail areas of turbine rotor wheels. The scanner is a power driven magnetic wheel device that is capable of completely rotating about the cylindrical surface between the wheels of the rotor. This surface may be that of a rotor shaft, a packing, or a wheel hub. While the surface of the shaft, packing or wheel hub may contain patterns of lands, grooves or surface erosion, an accurate radial position of the transducer is nevertheless maintained.

The scanner is built having a dimension so as to fit within a 1.75 inch gap between adjacent rotor wheels. It is electrically powered through a drive mechanism having magnetic wheels, which hold the device on the rotor surface by magnetic attraction. The scanner includes a mast on which are mounted radially adjustable holders for an ultrasonic transducer or other inspection probe and a rotary encoder.

BEST MODE FOR CARRYING OUT THE INVENTION

Integrated rotors, rotors machined from one piece of material whereby the rotor shaft and wheels are an integrated assembly, do not require tests that necessitate rotating the rotor as in non-integral rotors, However, the wheel dovetails do require inspection. Turbine integrated rotors are typically positioned on a stationary platform during testing or maintenance. The cost of renting, operating and maintaining power roller equipment for inspecting the wheel dovetails using test procedures that require rotation of the rotor is not justified. A scanner which provides a means for inspecting the wheel dovetails without rotating the turbine or rotor is provided by the invention.

Figure 1:
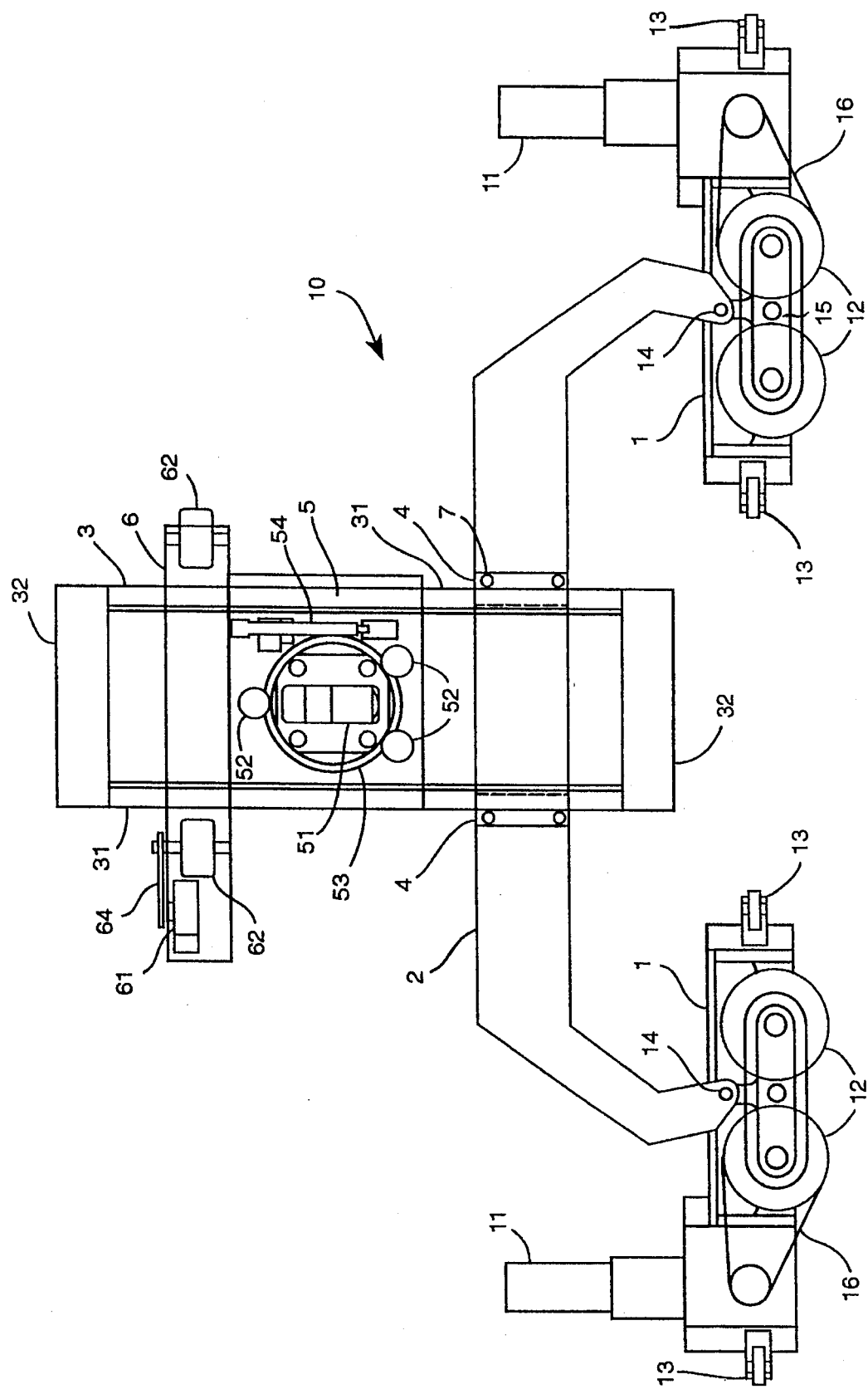
FIG. 1 shows a side view of the scanner.

As illustrated in FIG. 1, the scanner 10 comprises a pair of electric motor powered drive mechanisms or trolleys 1, a link beam 2 at the ends of which are connected the trolleys, and a mast 3 supported near the middle of the link beam. The mast is secured to the link beam by means of clamps 4 and supports a transducer holder 5 and an encoder holder 6 above the link beam.

Figure 2:
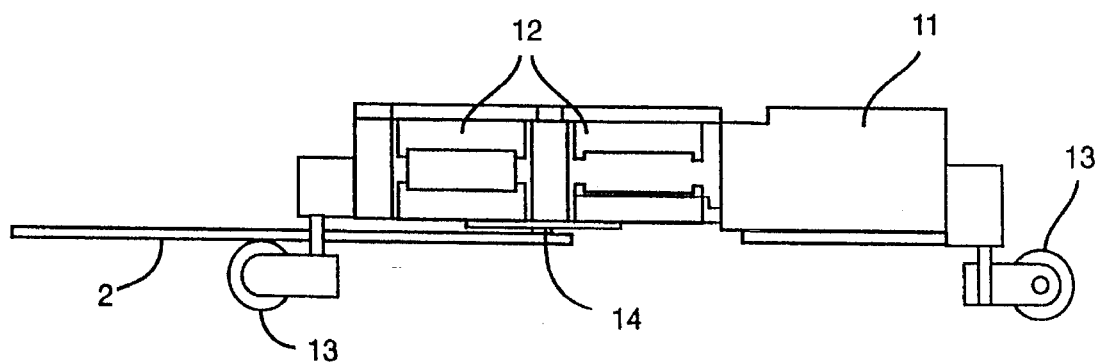
FIG. 2 shows a top view of a drive mechanism.

Each drive mechanism or drive unit 1 as seen in FIGS. 1 and 2 is comprised of a small, reversible d.c. electric motor 11 which is coupled via a belt 16 or other mechanism to permanent magnet wheels 12 carried by a truck 15. There are two permanent magnet wheels per truck, one of which is coupled to be driven by the electric motor 11 and the other is an idler wheel. The permanent magnet wheels are each comprised of two metal discs having sandwiched between them a rare earth permanent magnet disc. Each metal disc provides one of the poles of a magnet. The magnet wheels attract and hold the scanner to the cylindrical surface between the wheels of the rotor. Idler rollers 13 are attached at forward and aft ends of the trolley with their axis at 90 degrees to the axis of the magnet wheels to maintain the trolley at a predetermined distance from the vertical surface of a rotor wheel. Direct current is coordinately supplied through current limiting control means for operating the motors. The power source is located off-chassis at the control unit. It is possible to operate the scanner with only one of the trolleys being driven by a motor. However, it is advantageous that both trolleys be driven to prevent slippage and misalignment of the scanner, particularly at the 90 and 270 degree positions on the rotor.

The trucks 15 are pivotally attached at point 14 on the ends of the link beam 2. This allows the trolleys to follow the cylindrical surface of a rotor shaft or wheel hub. The separation of the trolleys by the link beam minimizes the effects of any rough surface. As would be apparent to those working in this field, the link beam 2 may be of other shapes than the one illustrated.

Clamped onto the link beam 2 by means of arm clamps 4 is a mast 3. Mast 3 is a frame formed by two elongated U-shaped channel members or arms 31 and end members 32. Each arm clamp 4 is secured to link beam 2 by bolts 7 and engages the interior side of one of the legs of a U-shaped channel member 31, thereby allowing limited radial positioning of the mast with respect to the link beam prior to tightening the bolts 7.

Figure 3:
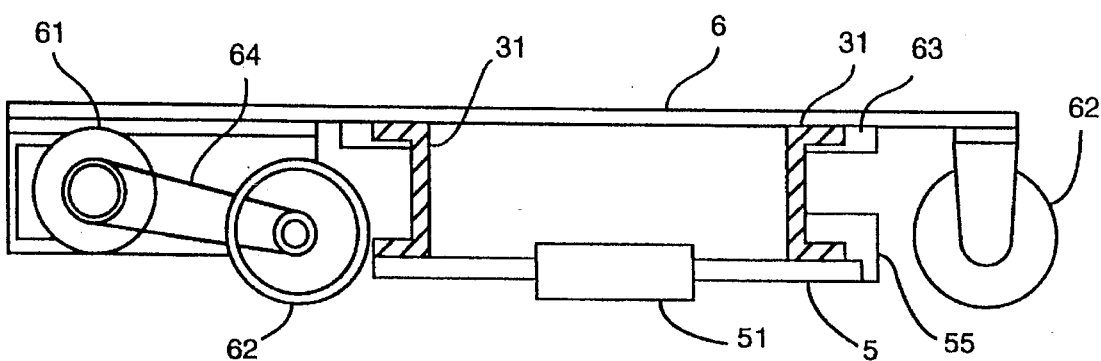
FIG. 3 shows a cross section view at the upper portion of the mast and also the encoder holder and the transducer holder secured to the mast.

The mast has releasably secured thereto a transducer holder 5 and an encoder holder 6. Transducer holder 5 and encoder holder 6 are attached to the U-shaped channel members 31 by clamping means 55 and 63, respectively, as illustrated in FIG. 3, and secured at the desired radially displaced location thereon, as for example, by set screws (not illustrated), so that the holders 5 and 6 are individually adjustable as well as replaceable.

Transducer holder 5 supports a transducer assembly comprised of an ultrasonic transducer 51 held in a gear ring 53. The gear ring can be rotated by gear drive mechanism 54. Once adjusted to the selected orientation, locking elements 52 are used to secure the ring and ultrasonic transducer in a fixed position. Releasing of the clamping element 55 that secures the transducer holder 5 to the mast permits the removal and installation of a replacement or different type of transducer. For scanning an adjacent wheel, the transducer holder with the transducer assembly may be mounted on the other side of the mast. As the skilled worker can appreciate, the manner in which the transducer holder is secured to the mast permits precise adjustments to be made to thereby allow focusing of the ultrasonic transducer in a true radial position, as well as in a skewed position for radial-axial type flaw examinations, In addition, the ultrasonic transducer has the ability to scan the ultrasonic beam in the radial direction.

The ultrasonic transducer is of a conventional design. Triggering signals, provided from an off-chasis control unit, trigger the emission of high frequency ultrasonic pulses from the transducer. These pulses are directed into the wheel at selected locations and echoes reflected from the wheel are detected and sent to the control unit for processing. The scanner may be moving or stationary during the transmitting of pulses and receiving of echoes.

Encoder holder 6 supports rotary encoder 61 and permanent magnet idlers 62. The permanent magnet idlers are not powered and are designed to ride on the vertical surface of the rotor wheel being inspected. This arrangement resists lateral pressures exerted by the ultrasonic transducer. Rotary encoder 61, driven by one of the permanent magnetic idlers via a drive belt 64, provides position feedback to the control unit as the scanner is powered around the rotor. By driving the rotary encoder from a position close to the transducer holder, any variation caused by surface roughness will be further minimized, An initial run around the shaft or hub is used to establish the encoder off-set with respect to the transducer, The position information provided by the rotary encoder is used in the data acquisition software to provide accurate inspection/location data.

Figure 4:
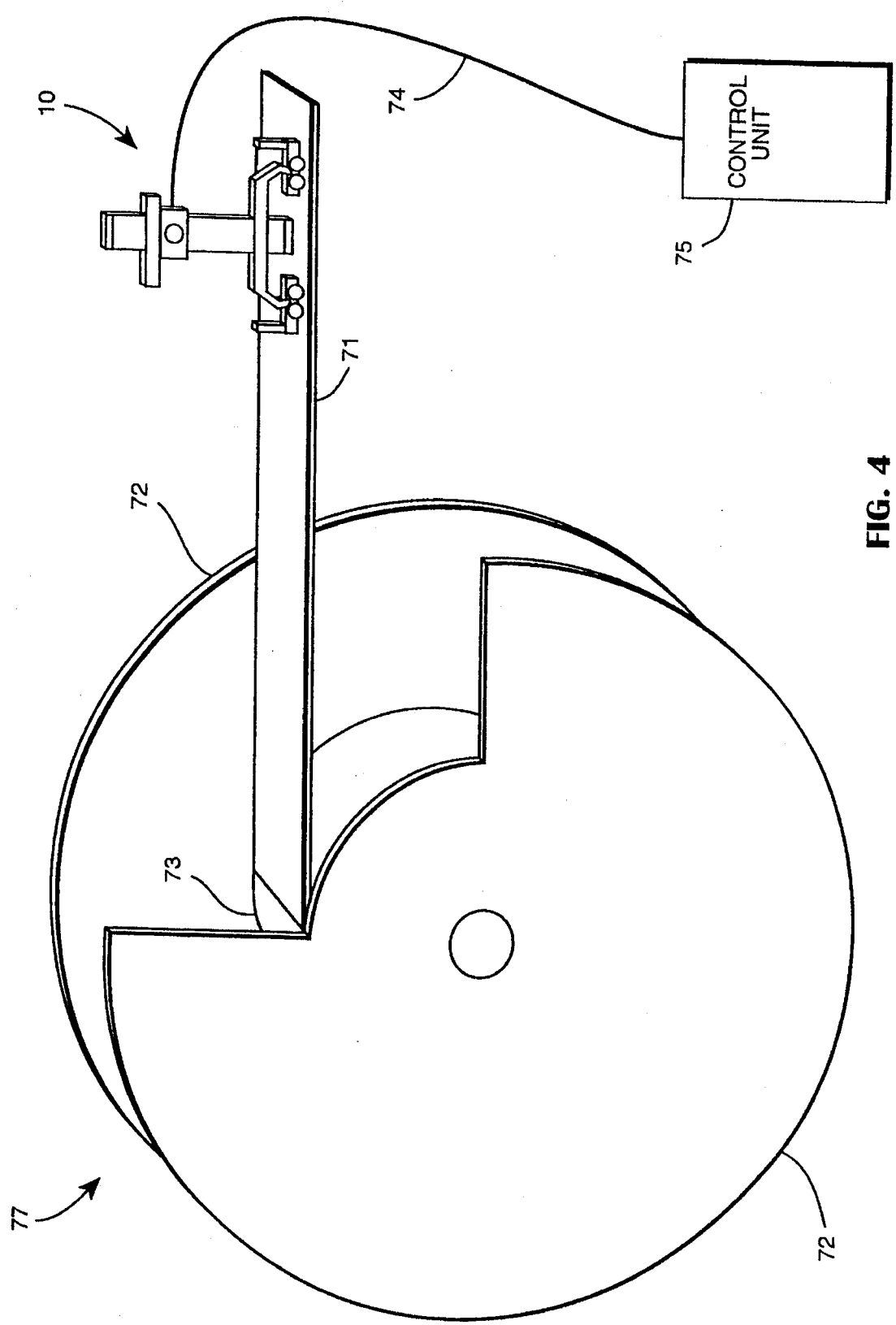
FIG. 4 shows means for inserting the scanner into the gap between rotor wheels.

Referring to FIG. 4, a blade or band 71 is used to facilitate the insertion into and removal of the scanner from the approximately 1.75 inch or larger gap between the rotor wheels 72 of turbine rotor 77. Blade 71 is placed in the gap in contact with the hub or shaft surface 73 so as to extend outwardly and the scanner 10 is placed on the blade. Control unit 75 provides power signals over wire bundle 74 and the scanner 10 is driven over the blade and into magnetic engagement with the surface 73 between the rotor wheels 72. The permanent magnet wheels of the scanner drive mechanisms I provide for magnetic attachment of the scanner to the cylindrical surface 73. Magnetic idlers on the encoder support maintain the mast at a predetermined distance from the vertical surface of the rotor wheel. The blade is removed and after an initial excursion around the surface 73 for initialization and calibration procedures, the scanner is powered around the surface 73, the dovetails are ultrasonically inspected and data related to the structure of the wheel dovetails are collected. Upon completion of the inspection procedure, the blade 71 is inserted in a manner to permit the driving of the scanner there onto and the scanner is retrieved by driving the magnetic wheels in reverse, causing the scanner to travel out of the rotor gap on the blade 71.

The scanner can be accommodated in rotors where the minimum gap between adjacent rotor wheels is at least 1.75 inch and is adaptable for use with rotor shafts having a diameter of 10–40 inches. The adjustability of the transducer support permits the ultrasonic transducer to be located at distances up to 100 inches radially from the rotor axial center line. The scanner may be adapted to any inspection procedure that requires 360 degree scans such as periphery, tenon, bucket covers and magnetic flux tests.

Inspection probes other than an ultrasonic transducer may be used with the scanner. Photo-optical inspection devices and cameras are alternative inspection probes.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A scanner comprising
    a link beam;
    a pair of trolleys, one each coupled to opposite ends of said link beam and having permanent magnet wheels, at least one of the trolleys including an electric motor for powering the trolley;
    a mast secured to a center portion of the link beam; and
    an inspection probe holder carrying an inspection probe attached to said mast.

2. A scanner as in claim I further comprising an encoder holder carrying an encoder attached to said mast.

3. A scanner as in claim 2 further including magnetic idlers mounted on said encoder holder, one of said idlers coupled to drive said encoder.

4. A scanner as in claim 1 wherein both of said trolleys include an electric motor for powering the respective trolleys.

5. A scanner as in claim 3 wherein both of said trolleys include an electric motor for powering the respective trolleys.

6. A scanner as in 4 wherein the trolleys further comprise idler rollers disposed on an axis at an angle of 90 degrees to the axis of the permanent magnet wheels.

7. A scanner as in claim 6 wherein the trolleys are pivotally coupled to said link beam.

8. A scanner as in claim 7 wherein the scanner has a width dimension of less than about 1.75 inch.

9. Apparatus for attaching to and rotating about a turbine rotor shaft surface between rotor wheels for inspecting dovetails of the rotor wheels comprising;
    a beam;
    a pair of drive mechanisms, each having permanent magnet wheels for attaching the apparatus to the rotor shaft surface, each drive mechanism including an electric drive motor;
    means for pivotally coupling one drive mechanism at one end of said beam and the other drive mechanism at the other end of said beam; and
    means for supporting a transducer assembly above the center portion of said beam.

10. Apparatus as in claim 9 further comprising means for supporting an encoder unit above the center portion of said beam.

11. Apparatus as in claim 10 wherein said means for supporting a transducer assembly and an encoder unit comprises a mast, said mast having a pair of spaced apart U-shaped channel members clamped to said beam, first means secured to one of said members for holding said transducer assembly and second means secured to said members for holding said encoder unit.

12. Apparatus as in claim 11 wherein said second means includes permanent magnet idlers for engaging a vertical surface of a rotor wheel.

13. Apparatus as in claim 12 wherein said first means and said second means are secured to said members by clamp means that permit their adjustment along said members.

14. Apparatus as in claim 12 wherein said permanent magnet wheels of said drive mechanisms comprise a rare earth permanent magnet.

15. A method for inspecting the rotor wheel dovetails of a turbine comprising the steps of:

inserting an inspection device having power driven permanent magnet wheels into the gap between adjacent rotor wheels and onto an exterior surface of the cylindrical rotor shaft, packing or wheel hub, said device being held on said cylindrical surface by magnetic attraction;

providing drive power to the magnet wheels to cause the device to rotate around said cylindrical surface;

controlling a radial position of said inspection device on said exterior surface;

triggering an ultrasonic transducer carried by said inspection device; and collecting data pertaining to the wheel dovetails.

16. A method as in claim 15 further comprising the steps of:

placing a band in the gap between the rotor wheels prior to inserting the inspection device;

inserting the inspection device by driving it along the band and onto the cylindrical surface; and removing the band prior to driving the inspection device around the rotor.

17. A method as in claim 16 further comprising the step of removing the device from the gap by: inserting the blade into the gap and driving the device onto the blade and out of the gap.

* * * * *